(12) United States Patent
Bengtsson

(10) Patent No.: US 9,619,625 B2
(45) Date of Patent: Apr. 11, 2017

(54) SYSTEM FOR OPTIMIZING A PATIENT'S DRUG DOSAGE REGIMEN OVER TIME

(75) Inventor: Henrik Bengtsson, Taastrup (DK)

(73) Assignee: Novo Nordisk A/S, Bagsvaerd (DK)

( * ) Notice: Subject to any disclaimer, the term of this patent is extended or adjusted under 35 U.S.C. 154(b) by 656 days.

(21) Appl. No.: 14/008,911

(22) PCT Filed: Mar. 29, 2012

(86) PCT No.: PCT/EP2012/055711
§ 371 (c)(1),
(2), (4) Date: Dec. 13, 2013

(87) PCT Pub. No.: WO2012/130992
PCT Pub. Date: Oct. 4, 2012

(65) Prior Publication Data
US 2014/0094743 A1    Apr. 3, 2014

Related U.S. Application Data

(60) Provisional application No. 61/471,389, filed on Apr. 4, 2011.

(30) Foreign Application Priority Data

Mar. 30, 2011    (EP) ..................................... 11160340

(51) Int. Cl.
*G06F 19/00*    (2011.01)
*A61M 5/24*    (2006.01)
(Continued)

(52) U.S. Cl.
CPC ........... *G06F 19/3468* (2013.01); *A61M 5/24* (2013.01); *G06F 19/3406* (2013.01);
(Continued)

(58) Field of Classification Search
CPC ............. G06F 19/3468; G06F 19/3456; G06F 19/3487; A61M 5/24
(Continued)

(56) References Cited

U.S. PATENT DOCUMENTS 5,593,390 A    1/1997    Castellano et al.
6,192,891 B1    2/2001    Gravel et al.
(Continued)

FOREIGN PATENT DOCUMENTS

CN    101308528 A    11/2008
EP    1048310 A2    11/2000
(Continued)

OTHER PUBLICATIONS

Sieh et al., WO 2010/009382, date: 2010.*
(Continued)

*Primary Examiner* — Manuel Mendez
(74) *Attorney, Agent, or Firm* — Wesley Nicolas

(57) ABSTRACT

A system for optimizing a patient's basal insulin dosage regimen over time, adapted to (a) determine from blood glucose values whether and by how much to vary a patient's present recommended amount of the insulin-containing drug in order to maintain the patient's future blood glucose level measurements within a predefined range, and (b) at the same time display blood glucose value data and the recommended amount data as a function of time.

8 Claims, 5 Drawing Sheets

(51) Int. Cl.
 *A61B 5/145* (2006.01)
 *A61M 5/31* (2006.01)

(52) U.S. Cl.
 CPC ...... *G06F 19/3456* (2013.01); *A61B 5/14532* (2013.01); *A61M 2005/3125* (2013.01); *A61M 2005/3126* (2013.01); *F04C 2270/041* (2013.01); *G06F 19/3487* (2013.01)

(58) Field of Classification Search
 USPC .................................. 604/65–67, 131, 151
 See application file for complete search history.

(56) References Cited

U.S. PATENT DOCUMENTS

| 6,302,855 | B1 | 10/2001 | Lav et al. |
| 7,133,329 | B2 | 11/2006 | Skyggebjerg et al. |
| 2003/0055323 | A1 | 3/2003 | Choi |
| 2003/0065536 | A1 | 4/2003 | Hansen et al. |
| 2003/0212379 | A1 | 11/2003 | Bylund et al. |
| 2004/0167464 | A1 | 8/2004 | Ireland et al. |
| 2005/0182358 | A1 | 8/2005 | Veit et al. |
| 2007/0239116 | A1 | 10/2007 | Follman et al. |
| 2009/0163793 | A1 | 6/2009 | Koehler et al. |
| 2009/0253970 | A1 | 10/2009 | Bashan et al. |
| 2010/0016700 | A1 | 1/2010 | Sieh et al. |
| 2010/0256047 | A1 | 10/2010 | Sieh et al. |

FOREIGN PATENT DOCUMENTS

| JP | 2002-531884 A | 9/2002 |
| JP | 2005-523426 A | 8/2005 |
| WO | 0013580 A1 | 3/2000 |
| WO | 03/047426 | 6/2003 |
| WO | 2005/046559 A2 | 5/2005 |
| WO | 2005/112554 A2 | 12/2005 |
| WO | 2009/027950 A2 | 3/2009 |
| WO | 2010/009382 A2 | 1/2010 |
| WO | 2010/052470 A1 | 5/2010 |
| WO | 2010/056718 A2 | 5/2010 |
| WO | 2010/098931 A1 | 9/2010 |

OTHER PUBLICATIONS

Ellis et al., WO 2010/052470, date:2010.*
Krulevitch et al., WO 2010/098931, date: 2010.*
Veit et al., WO 2005/046559, date:2005.*

* cited by examiner

SYSTEM FOR OPTIMIZING A PATIENT'S DRUG DOSAGE REGIMEN OVER TIME

CROSS-REFERENCE TO RELATED APPLICATIONS

This application is a 35 U.S.C. §371 National Stage application of International Application PCT/EP2012/055711 (published as WO 2012/130992), filed Mar. 29, 2012, which claimed priority of European Patent Application 11160340.3, filed Mar. 30, 2011; this application claims priority under 35 U.S.C. §119 of U.S. Provisional Application 61/471,389; filed Apr. 4, 2011.

The present invention generally relates to systems and methods allowing optimization and control of a patient's drug dosage regimen over time.

BACKGROUND OF THE INVENTION

In the disclosure of the present invention reference is mostly made to the treatment of diabetes by delivery of insulin, however, this is only an exemplary field of use for the present invention.

Type 2 diabetes is a progressive disease in which β-cell function deteriorates. Initiating therapy with oral agents is a reasonable approach to take with most patients, the exception being patients with extreme hyperglycemia (fasting plasma glucose >250 mg/dl). These patients require insulin to lower glucose levels. Otherwise, starting with oral therapy can be very effective, especially in patients with a short duration of diabetes and, thus, relatively adequate β-cell function. However, during the course of the disease many patients sooner or later will need therapy with insulin. When determining whether a patient should be put on insulin therapy, it is helpful to look to the guidelines for glycemic control. The American Diabetes Association (ADA) and American College of Endocrinology (ACE) publish goals for A1C, postprandial glucose, and fasting/pre-prandial glucose. Most patients who are unable to achieve these goals using oral agents are candidates for insulin therapy.

One type of initial insulin therapy for Type 2 diabetics is to use once-daily injections with a long-acting insulin such as Levemir® from Novo Nordisk, often in combination with oral antidiabetic agents. However, to be successful, insulin therapy requires timely and appropriate titration of dosages. For example, in combination with oral antidiabetic agents it is recommended to initiate Levemir treatment with once daily administration at a dose of 10 U or 0.1-0.2 U/kg. The dose of Levemir should then be titrated based on individual patients' needs, e.g. based on average (3-7 measurements) self-measured pre-breakfast BG values. For example, for a calculated value of >10.0 mmol/L it is recommended to adjust the Levemir dose with +8 units, for a calculated value of 9.1-10.0 mmol/L it is recommended to adjust the Levemir dose with +6 units, for a calculated value of 8.1-9.0 mmol/L it is recommended to adjust the Levemir dose with +4 units, for a calculated value of 7.1-8.0 mmol/L it is recommended to adjust the Levemir dose with +2 units, and for a calculated value of 6.1-7.0 mmol/L it is recommended to adjust the Levemir dose with +2 units. If one BG measurement is 3.1-4.0 mmol/L it is recommended to adjust the Levemir dose with −2 units, and if one BG measurement is <3.1 mmol/L it is recommended to adjust the Levemir dose with −4 units.

The calculation of the average pre-breakfast BG values as well as the resulting Levemir dose adjustments may either be performed by the patient him/herself or by a doctor/nurse based on BG values supplied by the patient. As appears, such a regimen is both time-consuming as well as prone to mistakes. This said, self-titration regimens are considered to facilitate empowerment of patients, allowing them to become more involved in their treatment which may then result in improved glycaemic control.

Correspondingly, devices and systems have been provided in which recommendations are generated based on self-measured BG values by a pre-programmed algorithm, e.g. corresponding to the relatively simple titration regimen described above. Indeed, much more sophisticated algorithms can be implemented taking into account e.g. patient characteristics and other variable inputs, see e.g. U.S. 2009/0253970. The algorithm may be in the form of software adapted to run on different platforms, e.g. PC, PDA or smartphone, or it may be embedded in a device such as a blood glucose meter (BGM), see e.g. U.S. 2010/0016700.

Although such automatically generated recommendations may be of great help to both medical staff and patients, the person responsible for the patient's diabetes treatment may be left uncertain about the recommendations made, just as it may be uncertain to what degree the patient actually uses the provided help.

Having regard to the above, it is an object of the present invention to provide systems and methods supporting cost-effective optimization and control of patient self-titration of a medical regimen.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in a first aspect of the invention a system for optimizing a patient's basal insulin dosage regimen over time is provided, comprising a patient unit and a display unit. The patient unit comprises a blood glucose meter for determining a blood glucose value from a blood sample, first controller and memory means adapted to (i) store data representing an initial basal insulin dosage regimen, the dosage regimen comprising a recommended amount of an insulin-containing drug to be taken at recommended intervals, (ii) determine from blood glucose values determined at a plurality of times whether and by how much to vary the patient's present recommended amount of the insulin-containing drug in order to maintain the patient's future blood glucose level measurements within a predefined range, (iii) create a blood glucose value log representing blood glucose values as a function of time, and (iv) create a recommended amount log representing recommended amounts as a function of time, the patient assembly further comprising means for transmitting log data to the display unit. The display unit comprises means for receiving log data from the drug delivery assembly, display means, and second controller and memory means adapted to (i) store the received log data, (ii) control the display means to at the same time display the blood glucose value log data and the recommended amount log data as a function of time. The patient unit could be in the form of a traditional BGM with imbedded software for making recommendations. The display unit could be in the form of a PC, e.g. for use by a medical practitioner, or a smart phone, e.g. for use by a patient, or any system comprising a display. Communication between the two units could be wired or wireless.

Thus, a system is provided in which dose-related information is created in the form of calculated recommendations, this without actual detection or recording of amounts expelled by a drug delivery device. By showing such dose recommendations and corresponding measured BG values at the same time the medical practitioner as well as the patient is given a tool which in a very simple and cost-effective way acquires and presents data which may help in optimizing the patient's titration progress. Further, by displaying suggested values together with actually measured BG values an opportunity is given to evaluate and investigate whether or not a patient actually adheres to the recommendations.

As appears, the concept of making recommendations is based on the assumption that the patient will actually administer the calculated and suggested dose amounts, however, after a given suggestion has been "used" it merely represents a calculated value based on historical data which in principle could be re-calculated later. Thus, if the receiving display unit is provided with the same data representing the patient's initial basal insulin dosage regimen, then only the BG log need to be transmitted to the display unit, the display unit being able to recalculate and display the recommendations.

Correspondingly, in a further aspect of the invention a system is provided comprising a patient unit and a display unit. The patient unit comprises a blood glucose meter for determining a blood glucose value from a blood sample, first controller and memory means adapted to (i) store data representing an initial basal insulin dosage regimen, the dosage regimen comprising a recommended amount of an insulin-containing drug to be taken at recommended intervals, (ii) determine from blood glucose values determined at a plurality of times whether and by how much to vary the patient's present recommended amount of the insulin-containing drug in order to maintain the patient's future blood glucose level measurements within a pre-defined range, and (iii) create a blood glucose value log representing blood glucose values as a function of time, the patient assembly further comprising means for transmitting log data to the display unit. The display unit comprises means for receiving log data from the drug delivery assembly, display means, and second controller and memory means adapted to (i) store the received log data, (ii) re-create based on the blood glucose value log a recommended amount log representing recommended amounts as a function of time, and (iii) control the display means to at the same time display the blood glucose value log data and the recommended amount log data as a function of time. The patient specific data used to recalculate the recommended amount log may be based on data received from the patient unit or data already stored in the display unit.

In an exemplary embodiment the system further comprises a drug delivery device comprising a drug reservoir or means for receiving a drug reservoir, an outlet for the drug, and an actuatable drug expelling mechanism for expelling drug from the reservoir and out through the outlet, as well as a cap releasably mountable on the drug delivery device and adapted to cover the outlet in a mounted position. In such an assembly the cap may comprise the blood glucose meter, the first controller and memory means, and the means for transmitting log data. In this way the patient is provided with a cap device which can be used as a simple add-on when adapted to be used with a specific type of drug delivery device, e.g. a traditional pen device.

The first controller and memory means may further be adapted to detect a cap-off event when the cap has been at least partially de-mounted from the drug delivery device for a predetermined amount of time, and create a cap-off log representing detected cap-off events as a function of time. Correspondingly, the second controller and memory means of the display unit may be adapted to control the display means to additionally display the cap-off time log as a function of time. By providing the cap with means for detecting when the cap has been at least partly removed from the drug delivery device a very simple and cost-effective way of collecting and displaying information indicative of actual use of the drug delivery is provided, this supporting the medical practitioner when evaluating the patient's log data.

In a further exemplary embodiment the drug expelling mechanism can be set to expel a desired dose of drug when actuated, the first controller and memory means being further adapted to detect the size of an expelled dose and create a dose log representing detected dose sizes as a function of time. Correspondingly, the second controller and memory means may be adapted to control the display means to additionally display the dose log as a function of time. Drug delivery devices provided with electronic means for detecting the amount of actually expelled drug are known, see e.g. WO 08/037801. Such a device may be adapted to transmit data to a cap device, e.g. wirelessly, optically or via galvanic contacts.

In the above disclosure of embodiments of the invention a system is described, however, the invention may also be in the form of a computer program (or software) adapted to be implemented on a computer system comprising controller means adapted to run such a computer program.

Correspondingly, in a further aspect of the invention a computer program is provided which, when run on a computer, will allow the computer to handle and control data as described above, i.e. receiving, displaying and calculating data.

In a system providing dosing recommendations based on BG measurements, it is also possible to detect whether or not the system has been used in the recommended way to deliver an amount of drug, this additional information can be used to improve the recommendations.

Correspondingly, in a further aspect of the invention a system for optimizing a patient's basal insulin dosage regimen over time is provided, comprising a blood glucose meter for receiving a patient blood sample and generating a blood glucose data set corresponding to a blood glucose value of the patient blood sample (e.g. BG value and time), detecting means for detecting when a patient-actuated operation is performed, the operation being indicative of the administration of a dose of an insulin containing drug, and memory means adapted to receive (a) blood glucose data sets corresponding to a plurality of blood glucose values as a function of time, (b) data representing detected patient-actuated operations as a function of time, and (c) data representing an initial basal insulin dosage regimen. The system further comprises a processor operatively connected to the memory means, the processor being programmed to determine from the blood glucose data sets determined at a plurality of times whether and by how much to vary a component in the patient's present insulin dosage regimen (i.e. to provide a recommendation) in order to maintain the patient's future blood-glucose-level measurements within a predefined range, and output means for communicating to the patient a component in the patient's insulin dosage regimen. In such a system a given blood glucose data set can then be disregarded by the processor if (i) the given blood glucose data set corresponds to a blood glucose value outside a predefined range, and/or (ii) no patient-actuated operation has been detected in a pre-defined amount of time prior to the generation of the given data set.

In an exemplary embodiment the system is in the form of a drug delivery assembly comprising a drug delivery device comprising a reservoir for a drug or means for receiving a reservoir, an outlet for the drug, a drug expelling mechanism for expelling drug from the reservoir and out through the outlet, and a cap device releasably mountable on the drug delivery device and adapted to cover the outlet in a mounted position. The cap device comprises the blood glucose meter, the memory means and the processor, the output means, and the detecting means, wherein the detection means is adapted to detect a cap-off event when the cap has been at least partially de-mounted from the drug delivery device for a predetermined amount of time. In this way the recommendation can take into account that the patient has not used the drug delivery device in accordance with the regimen. For example, if the patient is supposed to take an amount of Levemir at bed time, then failure to take off the cap e.g. in the time range 6:00 PM-2:00 AM prior to determining a morning BG would result in the algorithm disregarding the BG value when calculating a recommendation. If the cap does not comprise a real time clock then a time range relative to BG measurement could be defined.

In an alternative embodiment the drug expelling mechanism can be set to expel a desired dose of drug when actuated, the drug delivery device comprising controller and memory means adapted to detect the size of an expelled dose and create a dose log representing detected dose sizes as a function of time. When such log data is transmitted to the cap device they can be used to effectively calculate recommendations. In a further alternative embodiment both the BG meter and recommendation means are arranged in the drug delivery device per se.

Indeed, the above systems comprising detecting means for detecting when a patient-actuated operation is performed can also be utilized in the system comprising a display unit as described above.

In a yet further aspect of the invention there is provided a cap device releasably mountable on a drug delivery device of the above-described type and adapted to cover the outlet thereof in a mounted position. The cap device comprises a blood glucose meter for determining a blood glucose value from a blood sample, controller means adapted to (i) create a blood glucose value log representing blood glucose values as a function of time, (ii) detect a cap-off event when the cap has been at least partially de-mounted from a drug delivery device for a pre-determined amount of time, and (iii) create a time log representing detected cap-off events as a function of time, as well as means for transmitting the log data to an external receiver. The cap may be provided as a stand-alone add-on device or be provided as part of an assembly in combination with a drug delivery device as described above comprising a reservoir for a drug, an outlet for the drug, and a drug expelling mechanism for expelling drug from the reservoir and out through the outlet. The cap may be used in combination with a display unit adapted to show BG and cap-off data at the same time, thus providing an overview of the patient's compliance with a medical practitioner's recommendations.

The controller means of the invention may be in the form of a CPU or a microcontroller as well as their supporting components or any other configuration of electronic components suitable for the described functionality.

As used herein, the term "insulin" is meant to encompass any drug-containing flowable medicine capable of being passed through a delivery means such as a cannula or hollow needle in a controlled manner, such as a liquid, solution, gel or fine suspension, and which has a blood glucose controlling effect, e.g. GLP-1 and analogues thereof. In the description of the exemplary embodiments reference will be made to the use of insulin. Correspondingly, the term "subcutaneous" infusion is meant to encompass any method of transcutaneous delivery to a subject.

BRIEF DESCRIPTION OF THE DRAWINGS

In the following the invention will be further described with reference to the drawings, wherein.

In the figures like structures are mainly identified by like reference numerals.

DESCRIPTION OF EXEMPLARY EMBODIMENTS

When in the following terms such as "upper" and "lower", "right" and "left", "horizontal" and "vertical" or similar relative expressions are used, these only refer to the appended figures and not necessarily to an actual situation of use. The shown figures are schematic representations for which reason the configuration of the different structures as well as their relative dimensions are intended to serve illustrative purposes only.

Figure 1:
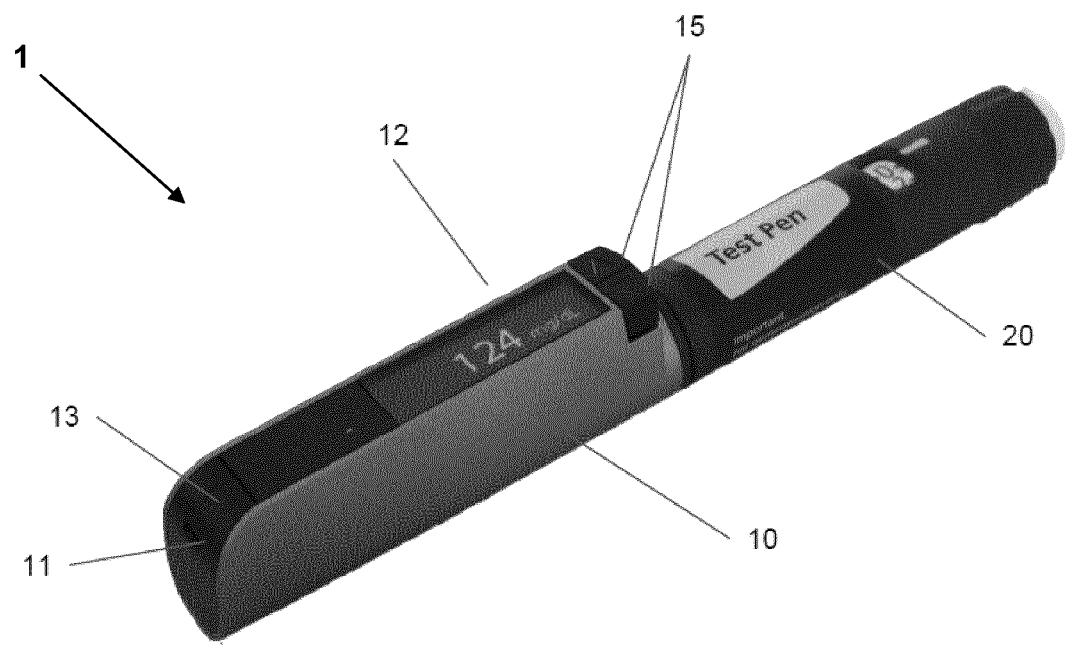
FIG. 1 shows a drug delivery device in combination with a mounted cap device.

FIG. 1 shows a drug delivery assembly 1 comprising a drug delivery device 20 containing an insulin formulation and onto which is mounted a cap device 10. The cap comprises a strip port 11 for a BGM arranged in the interior of the cap, a display 12 adapted to show BG values as well as other values (e.g. a LCD or OLED), an input button 13 adapted to confirm a given value, e.g. a BG reading, as well as a set of up/down buttons 15 adapted to scroll in a given log, e.g. a BG log. The cap further comprises means for detecting when it has been removed from the drug delivery device as well as a port for uploading data to an external device (not shown).

According to an aspect of the invention the shown cap further comprises processor and memory means for calculating a recommended change in drug delivery. For example, if the cap was adapted to support a patient during initial titration in a once-daily injection regimen with a long-acting insulin such as Levemir® from Novo Nordisk in combination with oral antidiabetic agents, then the cap device may be loaded with a simple algorithm corresponding the above-described titration guideline for Levemir®. For example, if the average of the 5 last BG measurements was 8.5 mmol/L the cap would recommend adjusting the Levemir dose with +4 units. The recommendation could be prompted and display in several ways. For example, the user may have to prompt the device to display the recommendation by using the input button in a specified way. As the titration dose regimen is based on fasting BG and bed-time injection of insulin, removing the cap from the drug delivery device may also be used to prompt the cap. The recommendation could be shown as "+4 total 24 units" this indicating both the change in dosing and the total amount of insulin to inject.

As the patient uses the cap device 10 logs are created storing logs of (accepted) BG values, dose size recommendations as well as cap-off events. The log may be based on either real or relative time. In the latter case the relative time stamps would be provided with absolute time stamps when transferred to an external device.

Figure 2:
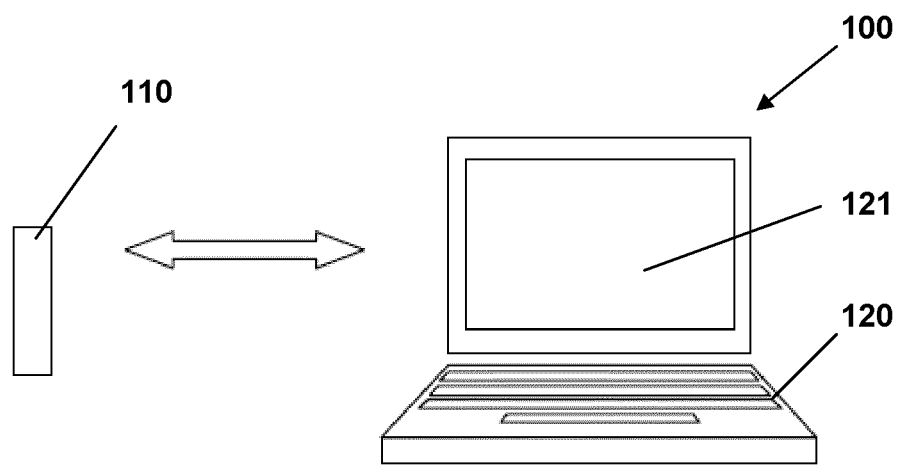
FIG. 2 shows a further cap device.

FIG. 2 shows a system 100 for optimizing a patient's basal insulin dosage regimen over time, and comprising a patient unit 110 and a display unit 120. The patient unit is in the form of a BFM cap device of the type shown in FIG. 1 and the display unit is in the form of a laptop computer. The shown units are adapted for wireless and bi-directional communication by e.g. RF such as Bluetooth, NFC or IR. Communication may be initiated by either device. Alternative communication may be by wire. When a patient is initiated on e.g. Levemir® patient specific parameters are uploaded to the cap device. Depending on how advanced the titration algorithm is more or less information will be needed, e.g. for a simple algorithm as described above the initial daily administration of a single dose of 10 U will be entered. As the patient uses the BGM cap BG and recommended dose data will be logged in the memory for subsequent upload to the PC when the patient comes to visit the doctor's office.

Figure 3:
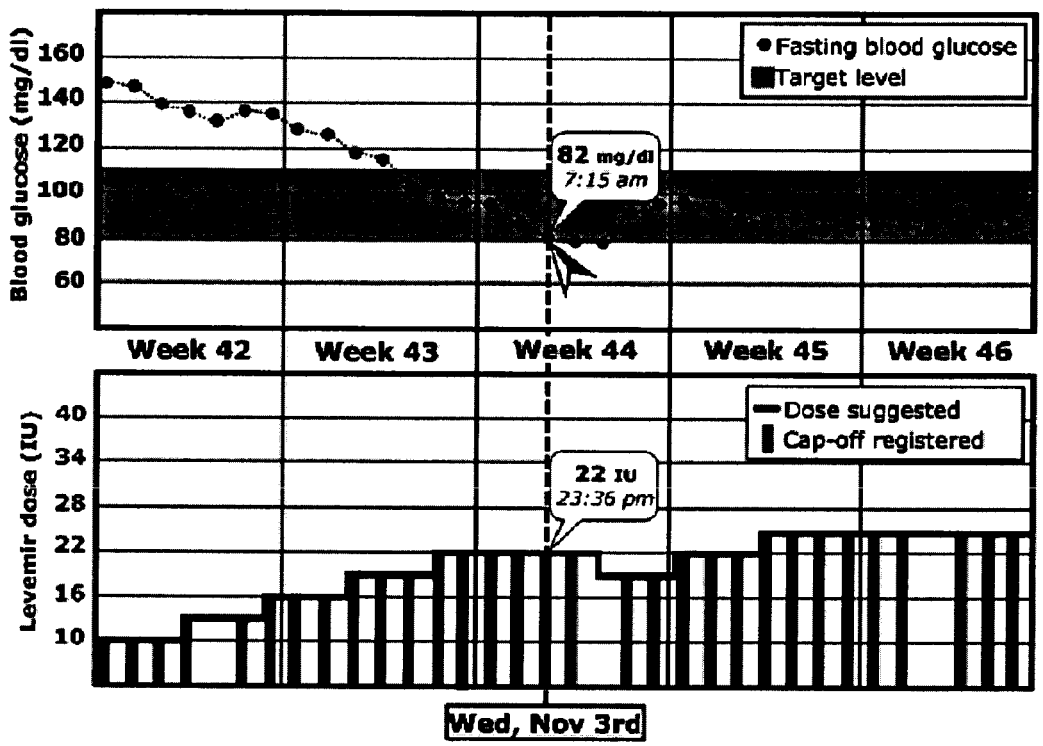
FIG. 3 shows a system for displaying information.

When the log data is uploaded to an external device such as a doctors' PC, the data may be displayed as shown in FIG. 3. As can be seen, the PC is provided with software presenting the BG values, recommendations and cap-off events as a function of time, each logged event being provided with an absolute time stamp. In this way a comprehensive overview is provided which can help the doctor evaluate the patient's titration regimen. The software is further adapted to provide statistic data and statistical analyses to further assist the doctor. Indeed, the same information could be uploaded to the patient's PC or to a smartphone.

Figure 4:
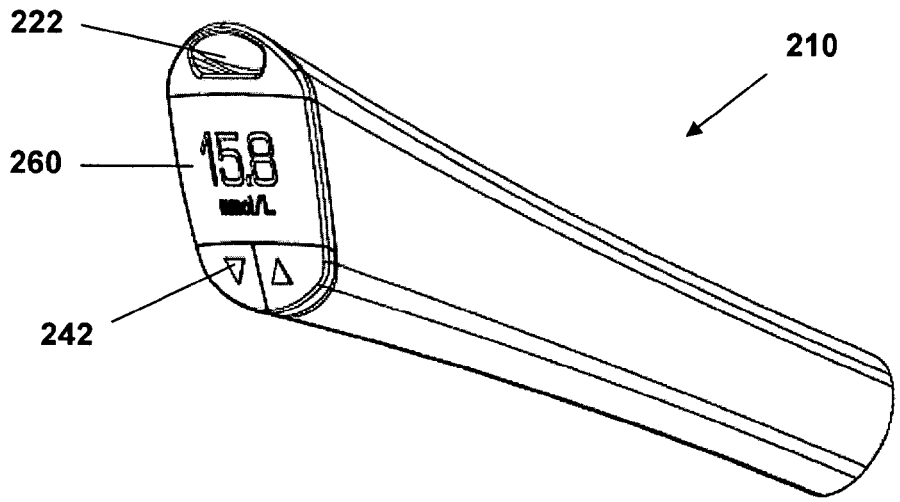
FIG. 4 shows graphs displaying patient information as a function of time.
Figure 5:
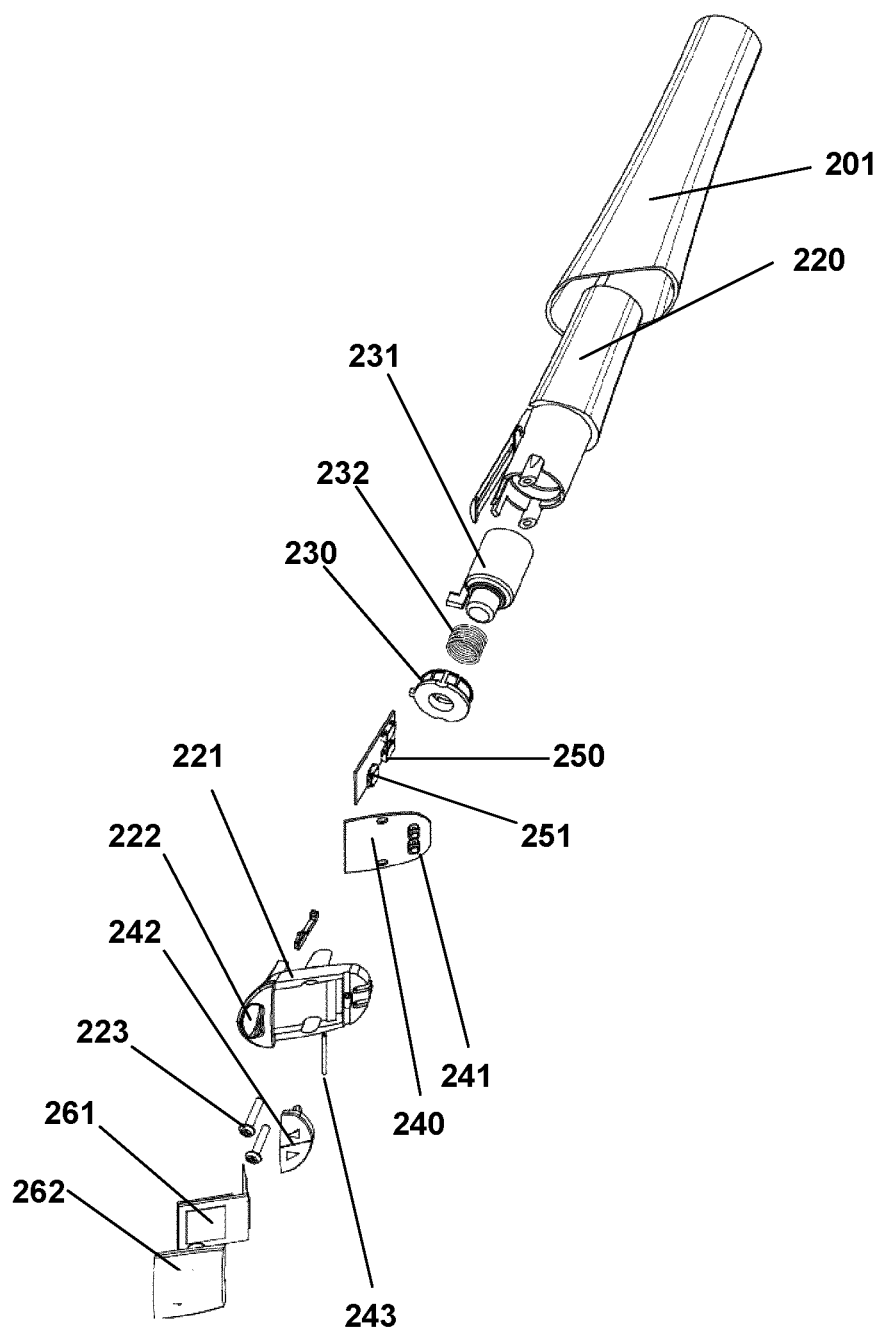
FIG. 5 shows an exploded view of the cap device of FIG. 2.

FIG. 4 shows an alternative configuration of a BGM cap 210 in which a strip port 222, a display 260 and user buttons 242 are arranged at the distal end of the cap. As seen in FIG. 5 the cap comprises a housing member 201 in which a generally tubular main chassis 220 is arranged, the latter having a top chassis 221 with a strip port 222 attached by screws 223. A spring support member 230 is attached to the main chassis. An actuator cup 231 is slidingly received in the main chassis in which it can travel between an un-loaded and a loaded position, the cup being biased towards its initial position by a spring 232 arranged between the spring support and the distal end of the cup, the cup being adapted to be moved distally when the cap is mounted on the distal end of a corresponding drug delivery device as seen in FIG. 1. The cap further comprises a first PCB 240 on which button switches 241 as well as an energy source and controller, memory and transmission means (not shown) are arranged, and a second PCB 250 on which cup-actuated switch means 251 and a BGM unit (not shown) are arranged. The switch means 251 is actuated when the cup 231 is moved axially thereby detecting a cap-off event. A display 261 is connected to the first PCB and covered by a transparent window member 262 attached to the top chassis to which further is attached two buttons 242 by means of an axel 243 allowing the buttons to pivot.

Figure 6:
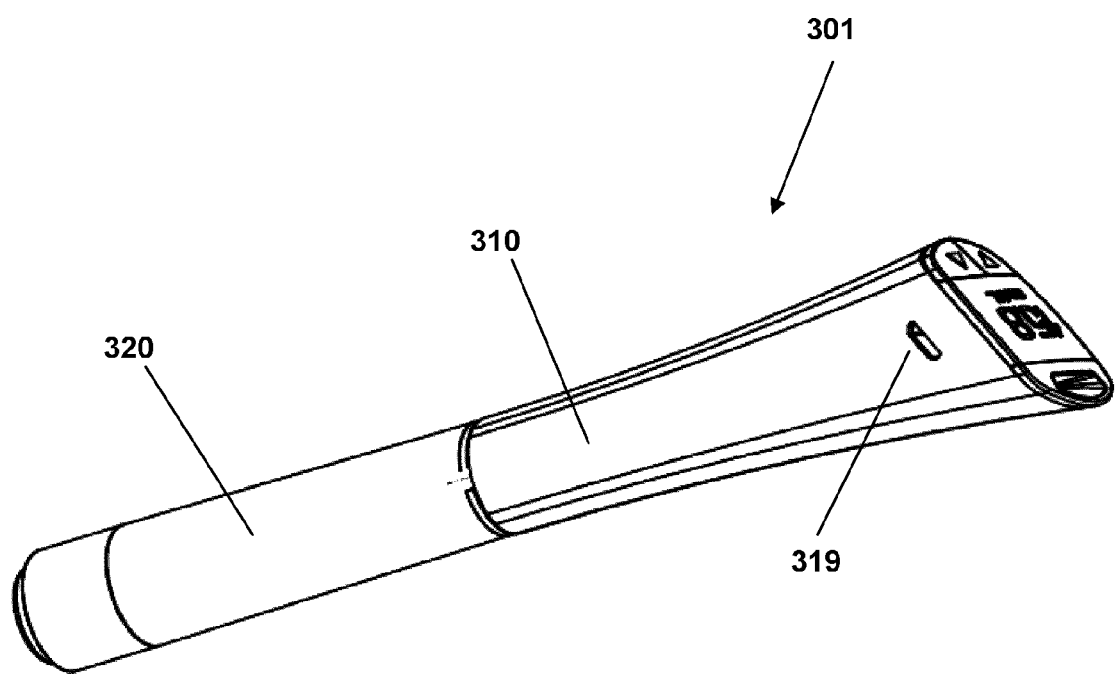
FIG. 6 shows a further cap device mounted on a drug delivery device.

FIG. 6 shows a drug delivery assembly 301 comprising a drug delivery device 320 of the type shown in FIG. 1 and onto which is mounted a cap device 310. The cap device is similar to the BGM cap device of FIG. 4, however, instead of wireless communication means the cap device is provided with an I/O port 319 adapted for wired communication.

In the shown embodiment of FIG. 1 the drug delivery device is a pre-filled pen device intended for single use only, however, the pen could also be a durable device intended to be used with exchangeable drug cartridges. In case the pen is of the durable type it may be provided with electronic means for detecting and creating a dose log which then could be transmitted to the cap device 10.

Figure 7:
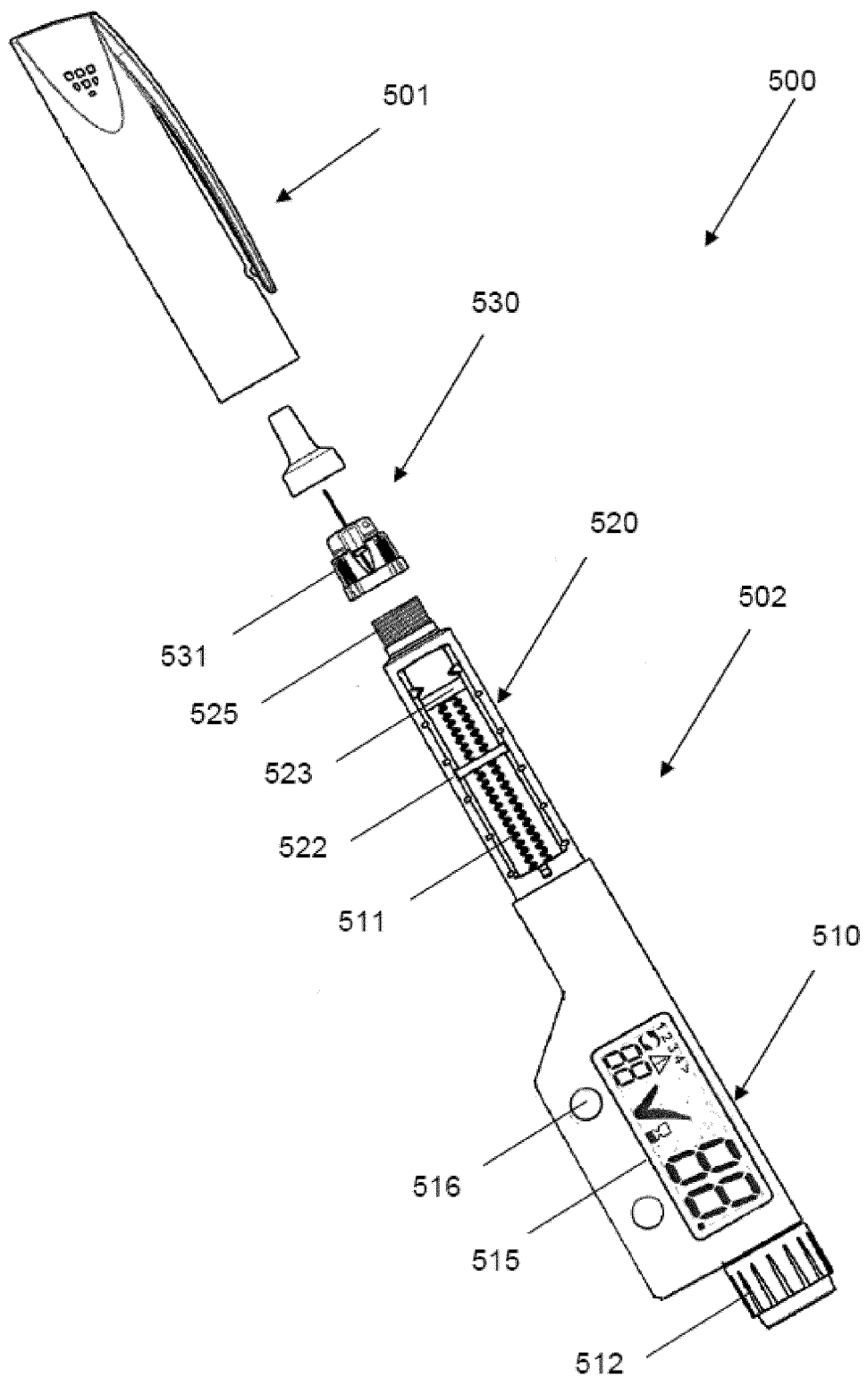
FIG. 7 shows a drug delivery means comprising electronic logging and display means.

FIG. 7 shows such a pen 500. The pen device comprises a cap portion 501 (here shown as a normal cap not related to the cap device 10) and a main portion 502 having a proximal part 510 in which a drug expelling mechanism is arranged, and a distal reservoir part 520 in which a replaceable drug-filled transparent cartridge 521 with a distal needle-penetratable septum is arranged and hold in place by a cartridge holder 522 releasably mounted to the proximal part, the cartridge holder having openings allowing a portion of the cartridge to be inspected. The cartridge is provided with a piston 523 driven by a piston rod 511 forming part of the expelling mechanism, the piston rod being adapted to be pushed back when a new cartridge is mounted. A proximal-most button 512 serves to manually set and expel a desired dose of drug. This type of a mechanical pen-formed drug delivery device is well known, see e.g. WO 99/38554 to which reference is made for further details in respect of the internal construction of the shown type of pen. The cartridge (or alternatively the cartridge holder) is provided with distal coupling means in the form of a hub mount 525 having, in the shown example, an external thread adapted to engage an inner thread of a hub 531 of a needle assembly 530. The proximal part further comprises a display 515, user actuatable keys 516 as well as electronic means (not shown) for detecting and storing information representing operations performed by the expelling mechanism. The detection means for detecting a set and/or expelled dose may be adapted to detect directly or indirectly the position of the piston rod, see e.g. U.S. Pat. No. 6,585,698 which is hereby incorporated by reference. The electronic means is adapted to store data representing injections performed by the user in the form of a time and dose log. The display may show the actual dose being set by a user using the button 512, the last dose (e.g. amounts of units expelled) and the time since last dose (or the actual time for the last dose), or the user may use the keys 516 to scroll through the log to display previous expelling data. The pen is adapted to transmit data to another system or device, which in the present context would be the cap device 10 of FIG. 1.

In the above description of the preferred embodiment, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:
1. A system for optimizing a patient's basal insulin dosage regimen over time, comprising a patient unit and a display unit, the patient unit comprising:
   a blood glucose meter for determining a blood glucose value from a blood sample,
   first controller and memory apparatus adapted to:
      store data representing an initial basal insulin dosage regimen, the dosage regimen comprising a recom- mended amount of an insulin-containing drug to be taken at recommended intervals, determine from blood glucose values determined at a plurality of times whether and by how much to vary the patient's present recommended amount of the insulin-containing drug in order to maintain the patient's future blood glucose level measurements within a predefined range, and create a blood glucose value log representing blood glucose values as a function of time, and structure to transmit log data to the display unit, the display unit comprising:

structure to receive the log data, display apparatus, second controller and memory apparatus adapted to:

store the received log data, and control the display apparatus to at the same time display the blood glucose value log data and a recommended amount log as a function of time.

2. A system as in claim 1, wherein the recommended amount log is calculated by the second controller and memory apparatus based on the received blood glucose value log.

3. A system as in claim 1, wherein the first controller and memory apparatus are adapted to create the recommended amount log, the recommended amount log representing recommended amounts as a function of time.

4. A system as in claim 1, further comprising:

a drug delivery device comprising:

a drug reservoir or structure to receive a drug reservoir, an outlet for the drug, and an actuatable drug expelling mechanism for expelling drug from the reservoir and out through the outlet, and a cap releasably mountable on the drug delivery device and adapted to cover the outlet in a mounted position.

5. A system as in claim 4, wherein the cap comprises the blood glucose meter, the first controller and memory apparatus, and the structure to transmit log data, the cap thereby forming the patient unit.

6. A system as in claim 4, wherein the first controller and memory apparatus is further adapted to:

detect a cap-off event when the cap has been at least partially de-mounted from the drug delivery device for a pre-determined amount of time, and create a cap-off log representing detected cap-off events as a function of time.

7. A system as in claim 6, wherein the second controller and memory apparatus is adapted to control the display apparatus to additionally display the cap-off time log as a function of time.

8. A system as in claim 4, wherein the drug expelling mechanism can be set to expel a desired dose of drug when actuated, the first controller and memory apparatus being further adapted to detect the size of an expelled dose and create dose log representing detected dose sizes as a function of time, and the second controller and memory apparatus is adapted to control the display apparatus to additionally display the dose log as a function of time.

* * * * *